(12) United States Patent
He et al.

(10) Patent No.: US 12,130,137 B2
(45) Date of Patent: Oct. 29, 2024

(54) BRILLOUIN-OCTA-SPECKLE MULTI-MODE ELASTOGRAPHY SYSTEM DEVICE

(71) Applicant: Nanchang Hangkong University, Nanchang (CN)

(72) Inventors: Xingdao He, Nanchang (CN); Jiulin Shi, Nanchang (CN); Yubao Zhang, Nanchang (CN); Zhongqi Hao, Nanchang (CN); Jin Xu, Nanchang (CN); Gang Shi, Nanchang (CN)

(*) Notice: Subject to any disclaimer, the term of this patent is extended or adjusted under 35 U.S.C. 154(b) by 183 days.

(21) Appl. No.: 18/150,203

(22) Filed: Jan. 5, 2023

(65) Prior Publication Data
US 2024/0035804 A1    Feb. 1, 2024

(30) Foreign Application Priority Data

Jul. 28, 2022  (CN) .......................... 202210894927.9

(51) Int. Cl.
*G01J 3/44* (2006.01)
*G01B 9/02091* (2022.01)

(52) U.S. Cl.
CPC ................................ *G01B 9/02091* (2013.01)

(58) Field of Classification Search
CPC .............. G01B 9/02091; A61B 5/0075; A61B 5/02007; A61B 5/0261; A61B 5/0066; G01J 3/44; G01N 21/47; G01N 21/01
See application file for complete search history.

(56) References Cited

U.S. PATENT DOCUMENTS 8,054,468 B2 * 11/2011 de Boer ............. G01N 21/4795
356/497

FOREIGN PATENT DOCUMENTS

CN          107764741 B  *  9/2019  ............. G01N 21/01

* cited by examiner

*Primary Examiner* — Abdullahi Nur
(74) *Attorney, Agent, or Firm* — Sandy Lipkin

(57) ABSTRACT

Disclosed is a Brillouin-optical coherence tomography angiography (OCTA)-speckle multi-mode elastography system device, including a Brillouin-OCTA sample scanning unit, a Brillouin scattering elastography system, an OCTA system, a speckle detection system, and a time sequence controller. According to the present invention, advantages that the Brillouin scattering elastography system can perform high-resolution measurement on a bulk elasticity modulus, the OCTA system can perform high-resolution structure imaging, and the speckle detection system can perform wide-field blood flow velocity measurement are utilized to perform in-situ synchronous imaging on a blood vessel structure and elasticity distribution, and to quantify a blood flow velocity, so that scientific basis and technical support are provided for early diagnoses of clinical blood vessel diseases.

8 Claims, 1 Drawing Sheet

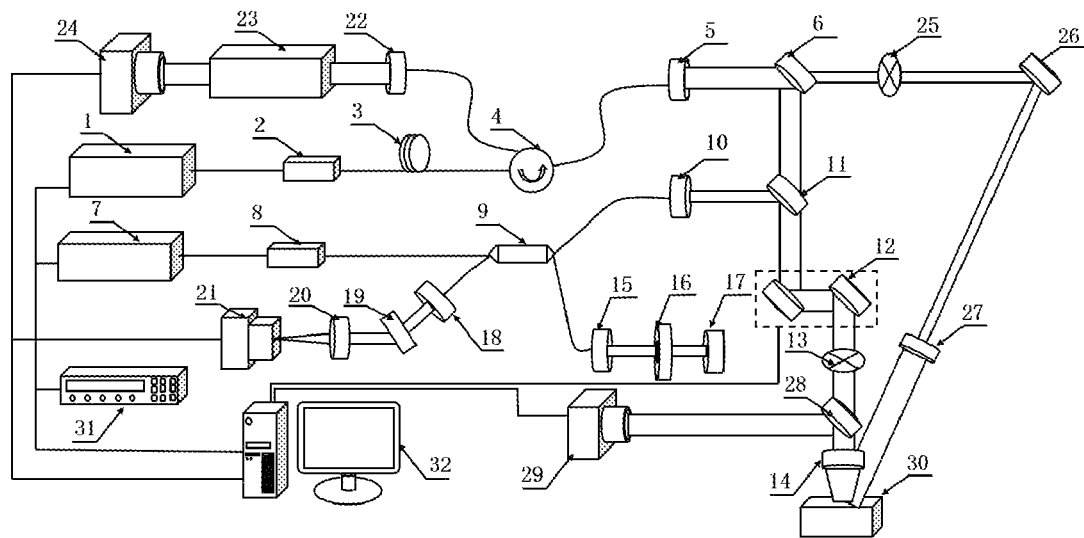

BRILLOUIN-OCTA-SPECKLE MULTI-MODE ELASTOGRAPHY SYSTEM DEVICE

BACKGROUND

1. Technical Field

The present invention relates to the technical field of elastography, and in particular to a Brillouin-optical coherence tomography angiography (OCTA)-speckle multi-mode elastography system device.

2. Description of Related Art

As a measurement system device, the present invention is principally configured to detect the elasticity and distribution, and to measure the blood flow velocity of a blood vessel by combining Brillouin scattering elastography, optical coherence tomography, and speckle imaging. The inventive concept lies in that the blood vessel is a pipeline for the heart to transport blood, and the blood vessel diseases mainly refer to atherosclerosis, inflammatory blood vessel diseases, functional blood vessel diseases, blood vessel true tumor diseases, etc. According to the results resulting from the pathological changes, the blood vessel diseases can be mainly divided into three types: (1) loss of blood vessel wall elasticity caused by lesions; (2) lumen narrowness caused by lesions; and (3) intravascular coagulation induced after the blood vessel intima is damaged by lesions, resulting in thrombosis. The structure and elasticity function of the blood vessel have already changed in the early stage of the blood vessel disease. Therefore, the high-resolution and rapid detection of the structure, elasticity, and blood flow velocity of the blood vessel is conducive to the early diagnosis and treatment of the blood vessel disease.

Brillouin scattering is an inelastic scattering process, having the spectral characteristics closely related to the properties of the medium (such as the density, viscosity, elasticity modulus, etc.). Therefore, the Brillouin scattering elastography technology can be employed to measure the bulk elasticity modulus of the blood vessel. The optical coherence tomography angiography (OCTA) obtains the tomographic image of the blood vessel distribution in the depth direction, depending on low-coherence interference, and thus can be employed to reconstruct the blood vessel distribution image through scanning. During speckle imaging, scattered particles on the tissue surface will backscatter the incident light. Different scattered lights has different optical path differences to the camera imaging plane, so that different scattered lights will form the random interference phenomenon on the image plane, which shows as a particle pattern having brightness changes in spatial distribution. The motion of scattered particles (red blood cells) causes the fluctuation of speckle intensity on the image plane. The information relevant with the motion velocity of the scattered particles can be obtained after the fluctuation is detected and analyzed. Therefore, by employing the Brillouin-OCTA-speckle multi-mode elastography system device, the elasticity and distribution of the blood vessel can be synchronously detected in situ, and the blood flow velocity of the blood vessel in a large area can be rapidly measured. Accordingly, the scientific basis is provided for the diagnosis and prevention of the blood vessel diseases.

SUMMARY

An objective of the present invention is to provide a Brillouin-optical coherence tomography angiography (OCTA)-speckle multi-mode elastography system device, to solve the technical problems in the prior art.

In order to realize the objective described above, the technical solution provided by the present invention is as follows: a Brillouin-OCTA-speckle multi-mode elastography system device includes a Brillouin-OCTA sample scanning unit, a Brillouin scattering elastography system, an OCTA system, a speckle detection system, and a time sequence controller, where the Brillouin scattering elastography system and the OCTA system share the Brillouin-OCTA sample scanning unit, the Brillouin scattering elastography system includes a Brillouin scattering signal excitation unit and a Brillouin signal acquisition unit, the OCTA system includes an OCTA signal excitation unit and an OCTA signal acquisition unit, the speckle detection system includes a speckle signal excitation unit and a speckle signal reception unit, and the Brillouin-OCTA sample scanning unit is composed of a dichroic mirror, a galvanometer set, a first optical shutter, and a scanning lens; where the Brillouin-OCTA sample scanning unit is configured to generate an OCTA signal and a Brillouin signal of a sample synchronously;

the Brillouin signal excitation unit is configured to excite a Brillouin scattering signal;

the Brillouin signal acquisition unit is configured to acquire a Brillouin spectrum signal to generate blood vessel elasticity information;

the OCTA signal excitation unit is configured to excite a light scattering signal;

the OCTA signal acquisition unit is configured to acquire an OCTA signal to generate blood vessel distribution information;

the speckle signal excitation unit is configured to excite a wide-field speckle signal; and the speckle signal reception unit is configured to acquire a speckle signal to generate blood flow relative velocity information.

Preferably, the Brillouin scattering signal excitation unit is composed of a narrow linewidth continuous laser, a first optical fiber isolator, an optical fiber delay line, an optical fiber circulator, a first collimator, and a beam splitter; the Brillouin signal acquisition unit is composed of a fifth collimator, a Brillouin spectrometer, and a first detector; and in the Brillouin elastography system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a reflected light passes through the dichroic mirror, the galvanometer set, and the first optical shutter, and is then focused on a sample to be detected by the scanning lens to interact with the sample to be detected to generate backward Brillouin scattering, and a backward Brillouin scattered light of the sample to be detected returns along an original path, and is output from port 3 of the optical fiber circulator, collimated by the fifth collimator, incident to the Brillouin spectrometer for frequency discrimination, and finally received by the first detector.

Preferably, the Brillouin scattering signal excitation unit enables excitation lights of the Brillouin scattering elastography system and the OCTA system to reach the dichroic mirror at the same time by adjusting the time sequence controller and the optical fiber delay line, so that the OCTA system and the Brillouin system scan the sample, and excite and acquire the blood vessel elasticity information and the blood vessel distribution information synchronously.

Preferably, the OCTA signal excitation unit is composed of an ultra-wideband light emitting diode, a second optical fiber isolator, a 2*2 optical fiber coupler, and a second collimator; the OCTA signal acquisition unit is composed of a reference arm, a grating spectrometer, and a linear array charge coupled device (CCD); and in the OCTA system, the ultra-wideband light emitting diode emits a light beam, the light beam is collimated by the second optical fiber isolator, the 2*2 optical fiber coupler, and the second collimator, and then reflected by the dichroic mirror, a reflected light passes through the galvanometer set and the first optical shutter, and is then focused on a sample to be detected by the scanning lens, and a backward scattered light generated through an interaction with the sample returns along an original path, is coherent with a light beam reflected by the reference arm, enters the grating spectrometer, and is finally acquired and received by the linear array CCD.

Particularly, the reference arm includes a third collimator, an attenuator, and a first plane reflector, and the grating spectrometer includes a fourth collimator, a grating, and a plano-convex lens.

Preferably, the speckle signal excitation unit is composed of a narrow linewidth continuous laser, a first optical fiber isolator, an optical fiber delay line, an optical fiber circulator, a first collimator, a beam splitter, a second optical shutter, a second plane reflector, and a beam expander; the speckle signal reception unit is composed of a scanning lens, a turnover reflector, and a second detector; and in the speckle detection system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a light beam transmitted through the beam splitter passes through the second optical shutter, the second plane reflector, and the beam expander, and is then incident on a sample to be detected, and a scattered signal generated through an interaction with the sample to be detected is reflected by the turnover reflector to the second detector through the scanning lens for detection.

Preferably, the speckle signal excitation unit enlarges a size of a light spot through the beam expander to excite a wide-field speckle signal at the sample.

Preferably, the speckle signal excitation unit and the Brillouin-OCTA sample scanning unit are alternately used by alternately using the first optical shutter and the second optical shutter.

Preferably, the Brillouin-OCTA sample scanning unit scans a surface X-Y of the sample through the galvanometer set, and surfaces X-Y at different depths of the sample by adjusting a height of the sample.

The present invention has the beneficial effects as follows:

According to the present invention, advantages that the Brillouin scattering elastography system may perform high-resolution measurement on a bulk elasticity modulus, the OCTA system may perform high-resolution structure imaging, and the speckle detection system may perform wide-field blood flow velocity measurement are utilized to perform in-situ synchronous imaging on a blood vessel structure and elasticity distribution, and to quantify a blood flow velocity, so that scientific basis and technical support are provided for early diagnoses of clinical blood vessel diseases.

BRIEF DESCRIPTION OF THE DRAWINGS

The accompanying drawings described herein are used for providing further understanding of the present invention, as a constitute part of the present invention. The illustrative examples of the present invention and the description thereof serve to explain the present invention, instead of limiting same improperly.

FIG. 1 shows a Brillouin-optical coherence tomography angiography (OCTA)-speckle multi-mode blood vessel elasticity and blood flow velocity measurement device according to the present invention.

REFERENCE NUMERALS

1—narrow linewidth continuous laser 2—first optical fiber isolator 3—optical fiber delay line 4—optical fiber circulator 5—first collimator 6—beam splitter 7—ultra-wideband light emitting diode 8—second optical fiber isolator 9—2*2 optical fiber coupler 10—second collimator 11—dichroic mirror 12—galvanometer set 13—first optical shutter 14—scanning lens 15—third collimator 16—attenuator 17—first plane reflector 18—fourth collimator 19—grating 20—plano-convex lens 21—linear array charge coupled device (CCD) 22—fifth collimator 23—Brillouin spectrometer 24—first detector 25—second optical shutter 26—second plane reflector 27—beam expander 28—turnover reflector 29—second detector 30—sample and 31—time sequence controller 32—computer.

DETAILED DESCRIPTION

The particular examples of the present invention are described in detail in this section, and the preferred examples of the present invention are shown in the accompanying drawings. The accompanying drawings are used to supplement the description of the text portion of the description with FIGURES, so that people can intuitively and vividly understand each technical feature and the overall technical solution of the present invention, but should not be interpreted as limiting the scope of protection of the present invention.

In the description of the present invention, several means one or more, a plurality of means two or more, greater than, less than, over, etc. are interpreted as excluding the recited number, and above, below, within, etc. are interpreted as including the recited number. The description of first and second, if any, is only for distinguishing between technical features, and should not be interpreted as indicating or implying relative importance or implicitly indicating the number or the sequential relation of technical features indicated.

With reference to FIG. 1, in the preferred example of the present invention, a Brillouin-optical coherence tomography angiography (OCTA)-speckle multi-mode elastography system device includes a Brillouin-OCTA sample scanning unit, a Brillouin scattering elastography system, an OCTA system, a speckle detection system, and a time sequence controller 31, where the Brillouin scattering elastography system, the OCTA system, and the speckle detection system share the Brillouin-OCTA sample scanning unit, the Brillouin scattering elastography system includes a Brillouin scattering signal excitation unit and a Brillouin signal acquisition unit, the OCTA system includes an OCTA signal excitation unit and an OCTA signal acquisition unit, the speckle detection system includes a speckle signal excitation unit and a speckle signal reception unit, and the Brillouin-OCTA sample scanning unit is composed of a dichroic mirror 11, a galvanometer set 12, a first optical shutter 13, and a scanning lens 14; where the Brillouin-OCTA sample scanning unit is configured to generate an OCTA signal and a Brillouin signal of a sample 30 synchronously;

the Brillouin signal excitation unit is configured to excite a Brillouin scattering signal;

the Brillouin signal acquisition unit is configured to acquire a Brillouin spectrum signal to generate blood vessel elasticity information;

the OCTA signal excitation unit is configured to excite a light scattering signal;

the OCTA signal acquisition unit is configured to acquire an OCTA signal to generate blood vessel distribution information;

the speckle signal excitation unit is configured to excite a wide-field speckle signal; and the speckle signal reception unit is configured to acquire a speckle signal to generate blood flow relative velocity information.

The preferred embodiment of the present invention may further have the following additional technical features:

In the present example, the Brillouin scattering signal excitation unit is composed of a narrow linewidth continuous laser 1, a first optical fiber isolator 2, an optical fiber delay line 3, an optical fiber circulator 4, a first collimator 5, and a beam splitter 6; the Brillouin signal acquisition unit is composed of a fifth collimator 22, a Brillouin spectrometer 23, and a first detector 24; and in the Brillouin elastography system, the narrow linewidth continuous laser 1 emits a light beam, the light beam passes through the first optical fiber isolator 2, the optical fiber delay line 3, port 1 of the optical fiber circulator 4, port 2 of the optical fiber circulator 4, and the first collimator 5, and is then split by the beam splitter 6, a reflected light passes through the dichroic mirror 11, the galvanometer set 12, and the first optical shutter 13, and is then focused on a sample 30 to be detected by the scanning lens 14 to interact with the sample 30 to be detected to generate backward Brillouin scattering, and a backward Brillouin scattered light of the sample 30 to be detected returns along an original path, and is output from port 3 of the optical fiber circulator 4, collimated by the fifth collimator 22, incident to the Brillouin spectrometer 23 for frequency discrimination, and finally received by the first detector 24.

In the present example, the Brillouin scattering signal excitation unit enables excitation lights of the Brillouin scattering elastography system and the OCTA system to reach the dichroic mirror 11 at the same time by adjusting the time sequence controller 31 and the optical fiber delay line 3, so that the OCTA system and the Brillouin system scan the sample 30, and excite and acquire the blood vessel elasticity information and the blood vessel distribution information synchronously.

In the present example, the OCTA signal excitation unit is composed of an ultra-wideband light emitting diode 7, a second optical fiber isolator 8, a 2*2 optical fiber coupler 9, and a second collimator 10; the OCTA signal acquisition unit is composed of a reference arm, a grating spectrometer, and a linear array charge coupled device (CCD) 21; and in the OCTA system, the ultra-wideband light emitting diode 7 emits a light beam, the light beam is collimated by the second optical fiber isolator 8, the 2*2 optical fiber coupler 9, and the second collimator 10, and then reflected by the dichroic mirror 11, a reflected light passes through the galvanometer set 12 and the first optical shutter 13, and is then focused on a sample 30 to be detected by the scanning lens 14, and a backward scattered light generated through an interaction with the sample 30 returns along an original path, is coherent with a light beam reflected by the reference arm, enters the grating spectrometer 19, and is finally acquired and received by the linear array CCD 21.

Particularly, the time sequence controller 31 is connected to the narrow linewidth continuous laser 1 and the ultra-wideband light emitting diode 7.

Particularly, the reference arm includes a third collimator 15, an attenuator 16, and a first plane reflector 17, and the grating spectrometer includes a fourth collimator 18, a grating 19, and a plano-convex lens 20.

In the present examples, the speckle signal excitation unit is composed of a narrow linewidth continuous laser 1, a first optical fiber isolator 2, an optical fiber delay line 3, an optical fiber circulator 4, a first collimator 5, a beam splitter 6, a second optical shutter 25, a second plane reflector 26, and a beam expander 27; the speckle signal reception unit is composed of a scanning lens 14, a turnover reflector 28, and a second detector 29; and in the speckle detection system, the narrow linewidth continuous laser 1 emits a light beam, the light beam passes through the first optical fiber isolator 2, the optical fiber delay line 3, port 1 of the optical fiber circulator 4, port 2 of the optical fiber circulator 4, and the first collimator 5, and is then split by the beam splitter 6, a light beam transmitted through the beam splitter 6 passes through the second optical shutter 25, the second plane reflector 26, and the beam expander 27, and is then incident on a sample 30 to be detected, a scattered signal generated through an interaction with the sample 30 to be detected is reflected by the turnover reflector 28 to the second detector 29 through the scanning lens 14 for detection.

Particularly, the speckle signal reception unit reflects the speckle signal through the turnover reflector 28 so as to acquire the signal when the speckle detection system detects the sample 30. When the speckle detection system does not work, a detection light of the Brillouin-OCTA sample scanning unit is transmitted through the turnover reflector 28 as well.

In the present embodiment, the speckle signal excitation unit enlarges a size of a light spot through the beam expander 27, so as to excite a wide-field speckle signal at the sample 30.

In the present example, the speckle signal excitation unit and the Brillouin-OCTA sample scanning unit are alternately used by alternately using the first optical shutter 13 and the second optical shutter 25.

In the present example, the Brillouin-OCTA sample scanning unit scans surfaces X-Y of the sample 30 at different depths by adjusting a height of the sample 30 through the galvanometer set 11.

A working process of the present invention is as follows: the speckle detection system, the Brillouin elastography system, and the OCTA system realize an alternate use of the speckle signal excitation unit and the Brillouin-OCTA sample scanning unit by alternately using the first optical shutter 13 and the second optical shutter 25 in combination with the turnover reflector 28. When the speckle detection system performs imaging, the first optical shutter 13 is closed, the second optical shutter 25 is opened, and the turnover reflector 28 is rotated into an optical path. After the light beam transmitted through the beam splitter 6 is expanded by the beam expander 27, the light spot is enlarged, and incident on the sample 30, so that wide-field scanning of the sample 30 may be realized, and the flow velocity of the blood vessel in a wide-field range may be measured. When the Brillouin optical elastography system and the OCTA system work, the first optical shutter 13 is opened, the second optical shutter 25 is closed, and the turnover reflector 28 is rotated out of the optical path. After passing through the Brillouin-OCTA sample scanning unit, backscattered signals are received by the Brillouin signal acquisition unit and the OCTA signal acquisition unit.

Particularly, detection on biological tissue is principally divided into three steps:

Step 1, the speckle detection system performs wide-field scanning on the sample 30 to measure the flow velocity of the blood vessel in the wide-field range. Details are as follows:

① When the speckle detection system performs wide-field scanning, the second optical shutter 25 is opened, and the speckle signal excitation unit is turned on; and the turnover reflector 28 is rotated into the optical path, and the speckle signal reception unit is turned on.

② On the speckle signal excitation unit, after passing through the second optical shutter 25, a light beam split by the beam splitter 6 is reflected by the second plane reflector 26, then incident to the beam expander 27 for beam expansion, and finally hit on the sample 30 in a form of a wide-field light spot to interact with the sample.

③ In the speckle signal reception unit, the speckle signal generated at the sample 30 is reflected by the turnover reflector 28 through the scanning lens 14 to enter the detector 29, so as to acquire the speckle signal, and the acquired signal is processed through a computer 32.

Step 2, the system is switched. The speckle detection system is turned off, and the Brillouin scattering elastography system and the OCTA system are turned on. Details are as follows:

The second optical shutter 25 is closed to block the light beam from entering the speckle signal excitation unit. The first optical shutter 13 is opened, and the turnover reflector 28 is rotated away from the optical path, so that the light beam behind the galvanometer set 12 may pass through the first optical shutter 13 and is then incident into the scanning lens 14.

Step 3, the Brillouin scattering elastography system and the OCTA system detect the sample at the same time, where the Brillouin scattering elastography system measures a bulk elasticity modulus of a blood vessel, and the OCTA system performs scanning to reconstruct a blood vessel distribution image. In order to realize synchronous detection of the two systems, the Brillouin optical elastography system and the OCTA system share the Brillouin-OCTA sample scanning unit. Details are as follows:

① The shared Brillouin-OCTA sample scanning unit principally includes the dichroic mirror 11, the galvanometer set 12, the first optical shutter 13, and the scanning lens 14, where the dichroic mirror 11 transmits the excitation light of the Brillouin scattering elastography system to enter the Brillouin-OCTA sample scanning unit, and reflects the excitation light of the OCTA system to enter the Brillouin-OCTA sample scanning unit, and the light beams entering the Brillouin-OCTA sample scanning unit are finally focused on the sample 30, to interact with the sample 30 to generate the scattered signal.

② In the Brillouin scattering signal excitation unit, a 780-nm excitation light released by the narrow linewidth continuous laser 1 passes through the first optical fiber isolator 2 and the optical fiber delay line 3, and then enters port 1 of the circulator 4. A spatial light output from port 2 of the circulator 4 is collimated by the first collimator 5, and split by the beam splitter 6, and part of the light enters the Brillouin-OCTA sample scanning unit.

③ On the OCTA signal excitation unit in the OCTA system, a 1310-nm excitation light released by the ultra-wideband light emitting diode 7 passes through the second optical fiber isolator 8 and the 2*2 optical fiber coupler 9, and is then collimated by the second collimator 10 to enter the Brillouin-OCTA sample scanning unit.

④ The time sequence controller 31 and the optical fiber delay line 3 are adjusted to control a time sequence of two lasers to ensure that light beams output by the two lasers reach the dichroic mirror 11 at the same time.

⑤ A signal light generated at the sample 30 returns from the Brillouin-OCTA sample scanning unit along the original optical path, and is acquired by the signal reception unit, where the Brillouin scattering elastography system and the OCTA system have independent signal reception units. In the Brillouin scattering signal reception unit, a backward Brillouin scattered signal generated at the sample 30 returns along the original optical path, passes through the optical fiber circulator 4, is then collimated by the fifth collimator 22, enters the Brillouin spectrometer 23, and undergoes spectral detection by the first detector 24, and an acquired spectral signal is processed through the computer 32.

⑥ In the OCTA signal acquisition unit, a backward scattered signal returning along the original path of the Brillouin-OCTA sample scanning unit is reflected by the dichroic mirror 11, passes through the second collimator 10 to enter the 2*2 optical fiber coupler 9, and is output by the fourth collimator 18. The output scattered signal is split by the grating spectrometer 19, then focused by the plano-convex lens 20 into the linear array CCD 21 for acquiring the signal, and the acquired signal is processed through the computer 32.

According to the present invention, advantages that the Brillouin scattering elastography system may perform high-resolution measurement on a bulk elasticity modulus, the OCTA system may perform high-resolution structure imaging, and the speckle detection system may perform wide-field blood flow velocity measurement are utilized to perform in-situ synchronous imaging on a blood vessel structure and elasticity distribution, and to quantify a blood flow velocity, so that scientific basis and technical support are provided for early diagnoses of clinical blood vessel diseases.

A person skilled in the art can combine and superimpose the additional technical features described above at random without conflict.

What are described above are only the preferred embodiments of the present invention, and the technical solutions that realize the objective of the present invention through basically the same means fall within the scope of protection of the present invention.

What is claimed is:

1. A Brillouin-optical coherence tomography angiography (OCTA)-speckle multi-mode elastography system device, comprising a Brillouin-OCTA sample scanning unit, a Brillouin scattering elastography system, an OCTA system, a speckle detection system, and a time sequence controller, wherein the Brillouin scattering elastography system and the OCTA system share the Brillouin-OCTA sample scanning unit, the Brillouin scattering elastography system comprises a Brillouin scattering signal excitation unit and a Brillouin signal acquisition unit, the OCTA system comprises an OCTA signal excitation unit and an OCTA signal acquisition unit, the speckle detection system comprises a speckle signal excitation unit and a speckle signal reception unit, and the Brillouin-OCTA sample scanning unit is composed of a dichroic mirror, a galvanometer set, a first optical shutter, and a scanning lens; wherein
    the Brillouin-OCTA sample scanning unit is configured to generate an OCTA signal and a Brillouin signal of a sample synchronously;
    the Brillouin signal excitation unit is configured to excite a Brillouin scattering signal;
    the Brillouin signal acquisition unit is configured to acquire a Brillouin spectrum signal to generate blood vessel elasticity information;
    the OCTA signal excitation unit is configured to excite a light scattering signal;
    the OCTA signal acquisition unit is configured to acquire an OCTA signal to generate blood vessel distribution information;
    the speckle signal excitation unit is configured to excite a wide-field speckle signal; and
    the speckle signal reception unit is configured to acquire a speckle signal to generate blood flow relative velocity information.

2. The Brillouin-OCTA-speckle multi-mode elastography system device according to claim 1, wherein the Brillouin scattering signal excitation unit is composed of a narrow linewidth continuous laser, a first optical fiber isolator, an optical fiber delay line, an optical fiber circulator, a first collimator, and a beam splitter; the Brillouin signal acquisition unit is composed of a fifth collimator, a Brillouin spectrometer, and a first detector; and in the Brillouin elastography system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a reflected light passes through the dichroic mirror, the galvanometer set, and the first optical shutter, and is then focused on a sample to be detected by the scanning lens to interact with the sample to be detected to generate backward Brillouin scattering, and a backward Brillouin scattered light of the sample to be detected returns along an original path, and is output from port 3 of the optical fiber circulator, collimated by the fifth collimator, incident to the Brillouin spectrometer for frequency discrimination, and finally received by the first detector.

3. The Brillouin-OCTA-speckle multi-mode elastography system device according to claim 2, wherein the Brillouin scattering signal excitation unit enables excitation lights of the Brillouin scattering elastography system and the OCTA system to reach the dichroic mirror at the same time by adjusting the time sequence controller and the optical fiber delay line, so that the OCTA system and the Brillouin system scan the sample, and excite and acquire the blood vessel elasticity information and the blood vessel distribution information synchronously.

4. The Brillouin-OCTA-speckle multi-mode elastography system device according to claim 1, wherein the OCTA signal excitation unit is composed of an ultra-wideband light emitting diode, a second optical fiber isolator, a 2*2 optical fiber coupler, and a second collimator; the OCTA signal acquisition unit is composed of a reference arm, a grating spectrometer, and a linear array charge coupled device (CCD); and in the OCTA system, the ultra-wideband light emitting diode emits a light beam, the light beam is collimated by the second optical fiber isolator, the 2*2 optical fiber coupler, and the second collimator, and then reflected by the dichroic mirror, a reflected light passes through the galvanometer set and the first optical shutter, and is then focused on a sample to be detected by the scanning lens, and a backward scattered light generated through an interaction with the sample returns along an original path, is coherent with a light beam reflected by the reference arm, enters the grating spectrometer, and is finally acquired and received by the linear array CCD.

5. The Brillouin-OCTA-speckle multi-mode elastography system device according to claim 1, wherein the speckle signal excitation unit is composed of a narrow linewidth continuous laser, a first optical fiber isolator, an optical fiber delay line, an optical fiber circulator, a first collimator, a beam splitter, a second optical shutter, a second plane reflector, and a beam expander; the speckle signal reception unit is composed of a scanning lens, a turnover reflector, and a second detector; and in the speckle detection system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a light beam transmitted through the beam splitter passes through the second optical shutter, the second plane reflector, and the beam expander, and is then incident on a sample to be detected, and a scattered signal generated through an interaction with the sample to be detected is reflected by the turnover reflector to the second detector through the scanning lens for detection.

6. The Brillouin-OCTA-speckle multi-mode elastography system device according to claim 5, wherein the speckle signal excitation unit enlarges a size of a light spot through the beam expander to excite a wide-field speckle signal at the sample.

7. The Brillouin-OCTA-speckle multi-mode elastography system device according to claim 5, wherein the speckle signal excitation unit and the Brillouin-OCTA sample scanning unit are alternately used by alternately using the first optical shutter and the second optical shutter.

8. The Brillouin-OCTA-speckle multi-mode elastography system device according to claim 1, wherein the Brillouin-OCTA sample scanning unit scans a surface X-Y of the sample through the galvanometer set, and surfaces X-Y at different depths of the sample by adjusting a height of the sample.

* * * * *